(12) United States Patent
Atehortua et al.

(10) Patent No.: US 7,935,523 B2
(45) Date of Patent: May 3, 2011

(54) APPARATUS FOR TEMPORAL IMMERSION CULTURE OF CELLS

(76) Inventors: Lucia Atehortua, Medellin (CO); David Vallejo, Medellin (CO); Esther Julia Naranjo, Medellin (CO); Sandra Milena Ceballos, Medellin (CO)

( * ) Notice: Subject to any disclaimer, the term of this patent is extended or adjusted under 35 U.S.C. 154(b) by 1016 days.

(21) Appl. No.: 11/625,817

(22) Filed: Jan. 22, 2007

(65) Prior Publication Data
US 2008/0176315 A1    Jul. 24, 2008

(51) Int. Cl.
*C12M 1/02* (2006.01)
(52) U.S. Cl. .................................. 435/294.1; 435/292.1
(58) Field of Classification Search ............... 435/294.1, 435/297.2, 299.1, 292.1
See application file for complete search history.

(56) References Cited

U.S. PATENT DOCUMENTS

| | | | |
|---|---|---|---|
| 6,190,913 B1 * | 2/2001 | Singh | 435/394 |
| 6,323,022 B1 * | 11/2001 | Chang et al. | 435/286.5 |
| 6,544,788 B2 * | 4/2003 | Singh | 435/383 |
| 6,566,126 B2 * | 5/2003 | Cadwell | 435/297.4 |

FOREIGN PATENT DOCUMENTS

| | | | |
|---|---|---|---|
| JP | 04158781 A | * | 6/1992 |
| SU | 1131899 A | * | 12/1984 |

* cited by examiner

*Primary Examiner* — William H Beisner
(74) *Attorney, Agent, or Firm* — John J. Martinez; Martinez Patents PC

(57) ABSTRACT

The present invention provides an apparatus for temporal immersion cell culture comprising: A first container for holding culture media; A second container for holding the culturing cells; At least, one tube that connects a port in the first container to a port in the second container; and, A mechanism to move cyclically the containers up and down wherein the culture media on the first container migrates by gravity to the second container when the first container is in a position higher than the second container, and wherein the culture media migrates back by gravity from the second container to the first container when the first container is in a position lower than the second container; and wherein the first container moves independently from the second container.

10 Claims, 4 Drawing Sheets

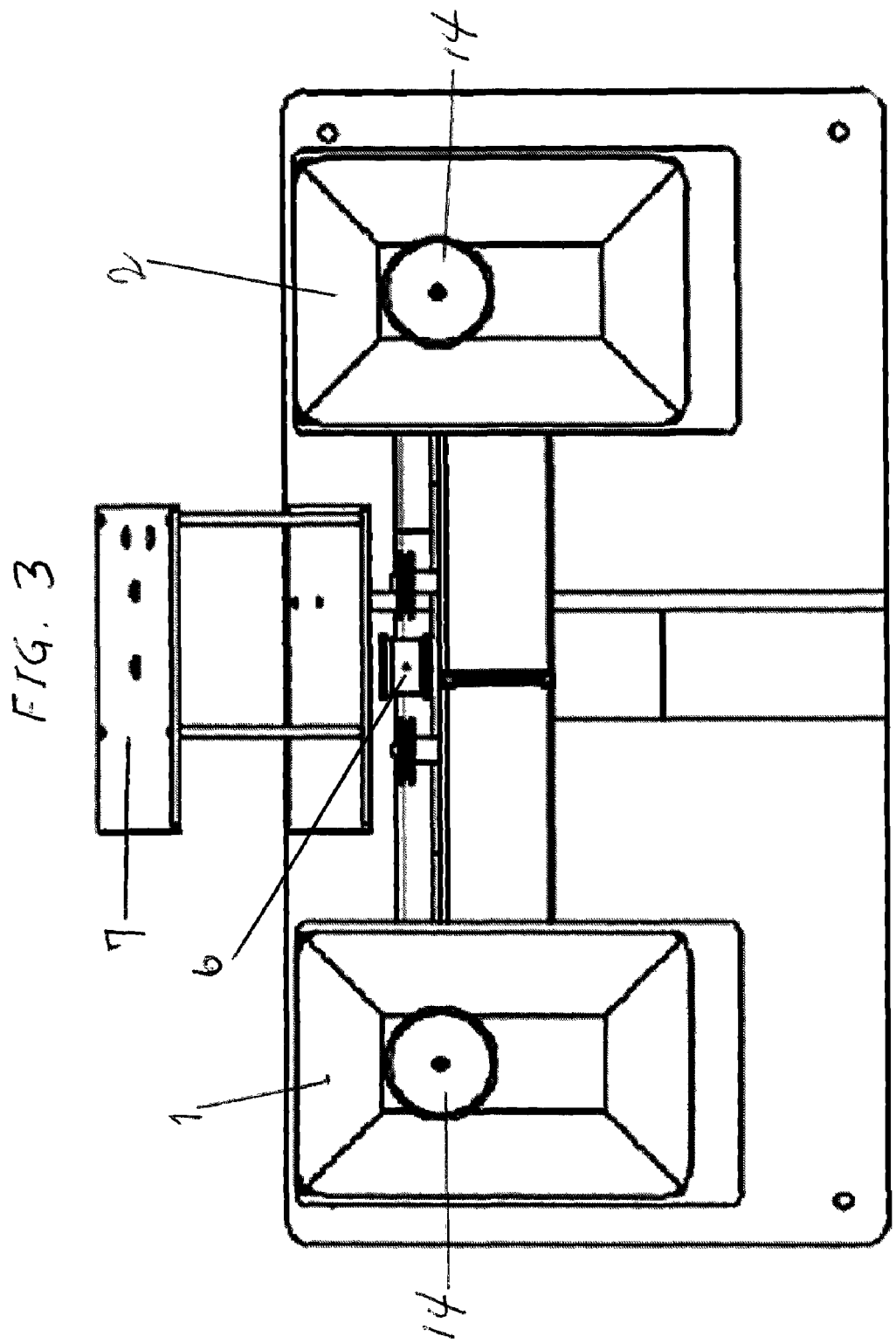

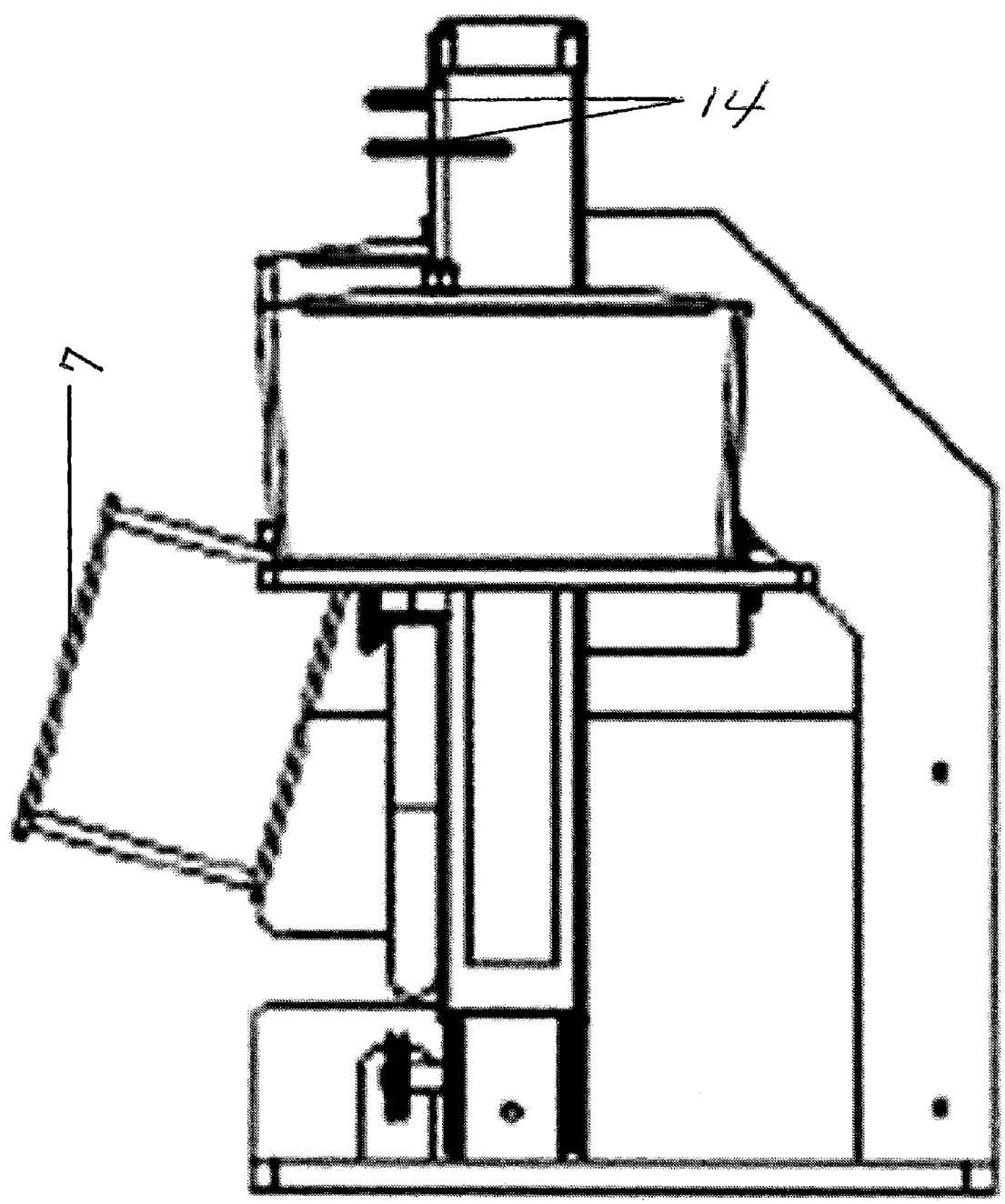

APPARATUS FOR TEMPORAL IMMERSION CULTURE OF CELLS

FIELD OF THE INVENTION

The apparatus of the present invention is related to temporal immersion culturing methods for animal cells, human cells, microbial organisms, insect cells, or plant cells. The apparatus of the present invention may also be used for temporal immersion culture of tissues, organs, plant embryos, plantlets or plants.

BACKGROUND OF THE INVENTION

Temporal immersion culture is an in vitro method in which cells, tissues, organs, plants embryos, plantlets or plants are grown by alternate cycles of temporal immersion in liquid culture media and appropriate aeration.

One of the temporal immersion culture methods described is the RITA® system (Etienne and Berthouly, *Plant cell, Tissue and Organ Culture*, 69:215 (2002)) which consist of an apparatus with a superior compartment vertically adjacent to an inferior compartment, wherein the superior compartment holds e.g., growing plants, and the inferior compartment holds culture media, wherein the culture media migrates temporarily to the superior compartment by the action of compressed air, and wherein the culture media migrates back to the lower compartment by gravity when the compressed air is turned off. This system has many parts and external connections, has a small surface area for culture, and forms bubbles and a humidity gradient.

Another temporal immersion culture system described in the literature consist of two separated compartments, one for e.g., plants and the other for culture media, wherein the culture media migrates from one compartment to another by the action of a pump (Espinosa, *Inform. Syst. Biotech. New Reports*, 2:7 (2002)). This system is big and hard to handle.

There are another temporal immersion system wherein a cylindrical container with e.g., growing plants, is rotated such that the plants rotating inside the rolling container get submerged in the culture media that lays in the inferior portion of the cylindrical container. This system has the limitation of shearing of the culturing elements that could be delicate and therefore damaged, e.g., a delicate layer of cells that is being cultivated.

Other temporal immersion systems consist of a container with horizontally adjacent compartments, wherein one compartment contains the elements to be cultured, e.g., plants or cells, and another compartment has the culture media, and wherein culture media migrates back and forth from one compartment to the other compartment by a rocking mechanism which causes the culture media to move from the temporarily upper compartment to the temporarily lower compartment because of gravity. These systems create a current from one compartment to the other compartment that is non-homogeneous and which may also cause shearing of the elements being cultivated. Examples of these systems are described in Publication No. MX PA04003837 A (Mexican Patent Application by Gus Petinovich, Leonardo, (2005)), U.S. Pat. No. 6,544,788 B2 by Singh, Vijay (2003), U.S. Pat. No. 6,190,913 B1 by Singh Vijay (2001), and U.S. Pat. No. 6,566,126 B2 by Cadwell, John (2003).

The present invention provides a versatile apparatus that overcomes the limitations of the described systems, wherein the present invention apparatus provides a system in which the cultured elements may be kept horizontally immobilized in an adequate sized surface, and wherein the immersion of the culture cells is made from the bottom to the top gently and homogeneous with appropriate aeration, without shearing nor bubbles formation, and without the use of air pressure nor pumps. The apparatus of the present invention can achieve the culture media immersion of the cultivated elements without any rocking. However, if rocking is desired after the immersion, the apparatus of the present invention may also be adapted for gently rocking.

SUMMARY OF THE INVENTION

The present invention provides an apparatus for temporal immersion cell culture comprising: A first container for holding culture media; A second container for holding the culturing cells on a solid mesh; At least, one tube that connects a port in the first container to a port in the second container; and, A mechanism to move the first container vertically and cyclically from a position higher than the second container to a position lower than the second container, and viceversa, wherein said mechanism may also move the second container vertically and cyclically from a position higher than the first container to a position lower than the first container, and viceversa; wherein the culture media on the first container migrates by gravity to the second container when the first container is in a position higher than the second container, and wherein the culture media migrates back by gravity from the second container to the first container when the first container is in a position lower than the second container; and wherein the first container moves independently from the second container.

In one aspect of the apparatus of the present invention, the mechanism moving the first container and the second container, vertically and cyclically, moves both containers independently in a synchronized way such that when one container is up, the other container is down, and viceversa.

In another aspect of the apparatus of the present invention, both, the first container and the second container always maintain a horizontally fixed axis position, without tilting from said horizontally fixed axis position when both containers move vertically and cyclically.

However in an alternative embodiment, the apparatus of the present invention may have a device to rock-tilt one or both containers along the horizontal axis while the container that is rocked-tilted also moves vertically and cyclically.

In another aspect of the apparatus of the present invention, the apparatus is used to culture animal cells, human cells, insect cells, microbial cells and plant cells. In addition, said apparatus may be used to culture tissues, organs, plant embryos, plantlets and plants.

In another aspect of the present invention, the apparatus comprises a control module to govern the mechanism that moves vertically and cyclically the first container and the second container.

In a further aspect of the apparatus of the present invention, the first container and the second container have respective filters, wherein the filter of each container allows proper aeration, while filtering microscopic contamination.

In one more aspect of the apparatus of the present invention, both, the first container and the second container, have walls made of a material which is fully transparent to light.

However, in a different embodiment of the apparatus of the present invention, at least one of the two containers, has walls that completely block light passing through said walls, and wherein the container with walls that block passing light is illuminated inside with a source of light with a determined wave length, and wherein all internal surfaces of the container with walls that block passing light are surfaces with the characteristics of a mirror.

In an additional optional aspect of the apparatus of the present invention, the tube that connects the port of the first container to the port of the second container has a filter that allows culture media to pass through, but blocks possible contaminants.

Objectives and additional advantages of the present invention will become more evident in the description of the figures, the detailed description of the invention and the claims.

BRIEF DESCRIPTION OF THE DRAWINGS

FIG. 3. shows a superior view of the preferred embodiment of the apparatus of the present invention.

FIG. 4. shows a lateral view of the preferred embodiment of the apparatus of the present invention.

DETAILED DESCRIPTION OF THE INVENTION

Figure 1:
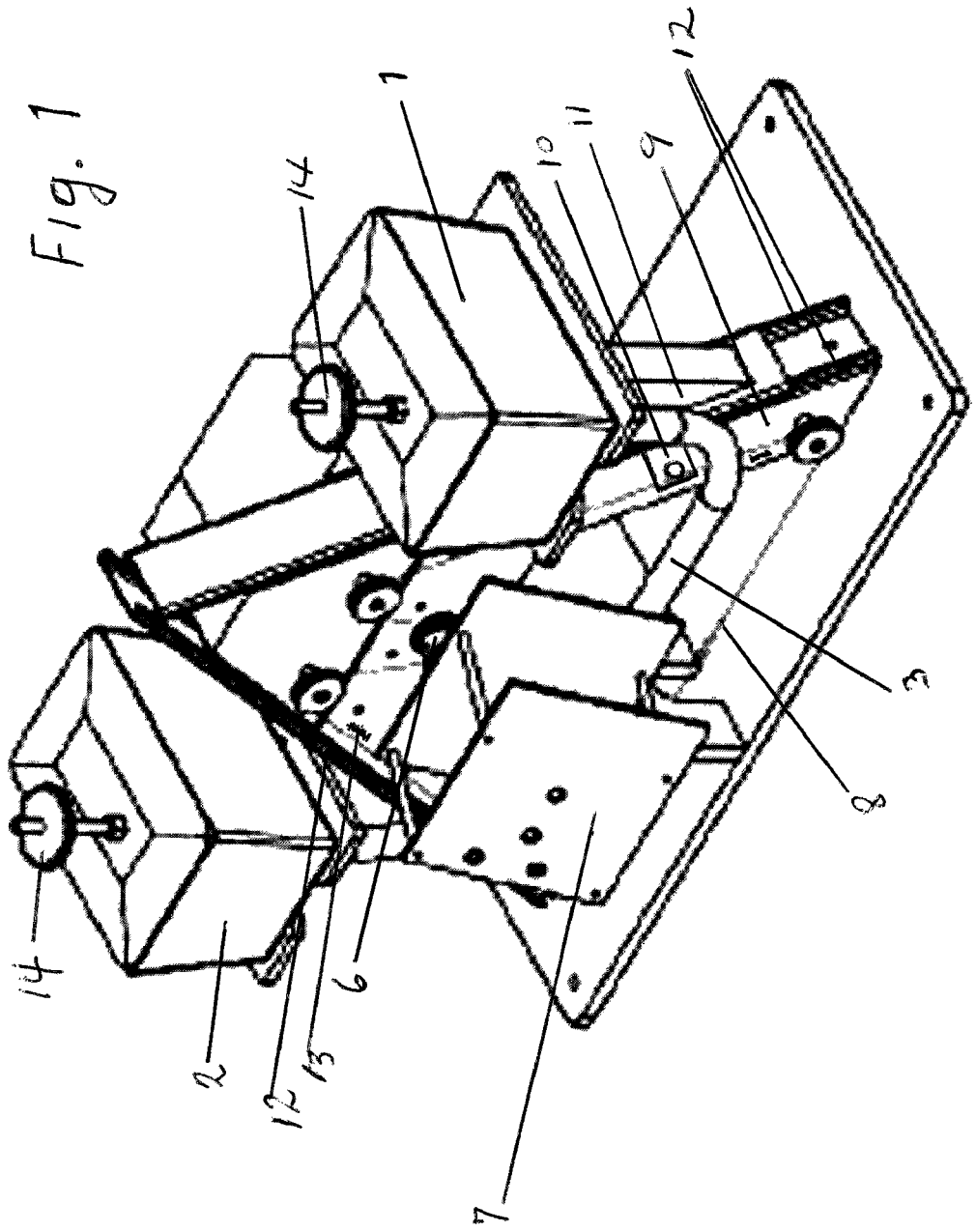
FIG. 1. shows a tridimensional illustration of the preferred embodiment of the apparatus of the present invention.

The object of the present invention is to provide an apparatus (FIG. 1.) for temporal immersion cell culture comprising: A first container (1) for holding culture media; A second container (2) for holding the culturing cells; At least, one tube (3) that connects a port (4) (FIG. 2.) in the first container (1) to a port (5) (FIG. 2.) in the second container (2); and, A mechanism to move the first container (1) vertically and cyclically from a position higher than the second container (2) to a position lower than the second container (2), and viceversa, wherein said mechanism may also move the second container (2) vertically and cyclically from a position higher than the first container (1) to a position lower than the first container (1), and viceversa; wherein the culture media on the first container (1) migrates by gravity to the second container (2) when the first container (1) is in a position higher than the second container (2), and wherein the culture media migrates back by gravity from the second container (2) to the first container (1) when the first container (1) is in a position lower than the second container (2); and wherein the first container (1) moves independently from the second container (2).

In one aspect of the apparatus of the present invention, the mechanism moving the first container (1) and the second container (1), vertically and cyclically, moves both containers (1,2) independently in a synchronized way such that when one container is up, the other container is down, and viceversa.

In a preferred embodiment of the present invention, culturing cells are laid over an horizontal elevated solid mesh (no shown) made of non-toxic material inside the second container (2) to allow a tridimensional immersion of the culturing cells in culture media.

In another aspect of the present invention, the apparatus comprises a control module (7) (FIGS. 1-4) to govern the mechanism that moves vertically and cyclically the first container (1) and the second container (2).

Figure 2:
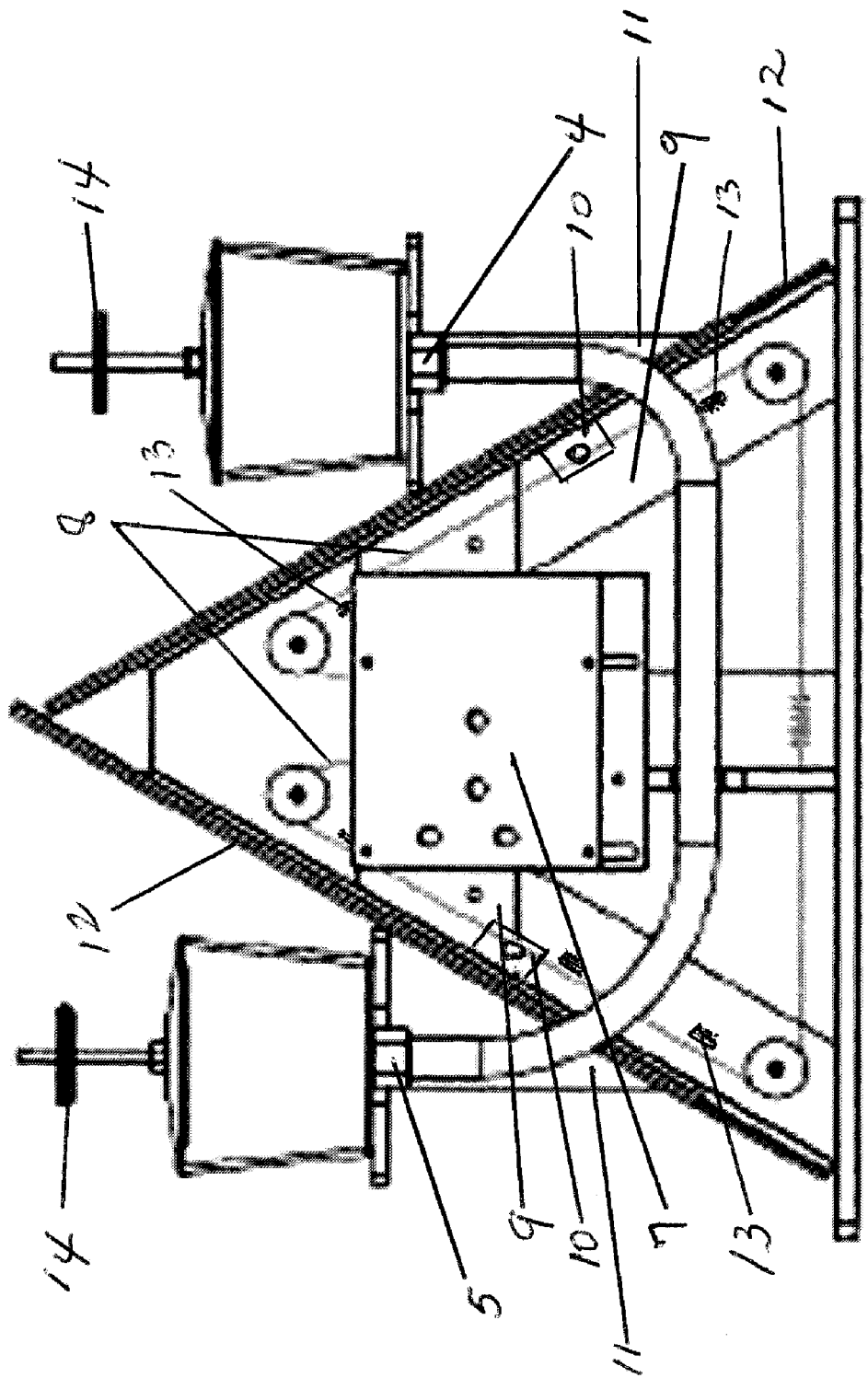
FIG. 2. shows a frontal view of the preferred embodiment of the apparatus of the present invention.

In a preferred embodiment of one aspect of the present invention, the mechanism to move the first container (1) and the second container (2) is constituted by an electric powered direct current motor (6) (FIGS. 1. and 3.), that is governed by a control module (7) (FIGS. 1-4). The motor (6) powers a wire (8) (FIGS. 1-2) that runs over an inverted V frame (9) (FIGS. 1-2). The wire (8) is attached to arm appendages (10) (FIGS. 1-2) that are connected to supports (11) (FIGS. 1-2) for the first container (1) and the second container (2). The supports (11) for the first container (1) and the second container (2) fit on top of tracks (12) (FIGS. 1-2) laid down over the lateral surfaces of the diagonal extensions of the inverted V frame (9). As the motor (6) powers the wire (8), the wire pulls the containers (1,2) through the arm appendages (10) connected to the supports (11) which move along the tracks (12). The movement of the wire (8) depends on the motor (6) which is governed by the control module (7), wherein the control module (7) can be programmed for number, frequency and duration of cycles. The control module (7) directs movement in alternate directions as well as the stationary periods of each cycle. The control module receives inputs from sensors (13) (FIGS. 1-2) located along the tracks to determine position and movement distance.

A cycle is defined as any combination of up and down vertical movements and determined duration stationary periods.

In addition to the preferred mechanism to move the containers, said mechanism can also be any hydraulic, pneumatic, electric or mechanical type or any combination of these.

The present invention allows a set up of several apparatus functioning in series that are controlled by a computer.

In the preferred embodiment of the apparatus of the present invention, both, the first container (1) and the second container (2) always maintain a horizontally fixed axis position, without tilting from said horizontally fixed axis position when both containers (1,2) move vertically and cyclically.

However in an alternative embodiment, the apparatus of the present invention may have a device to rock-tilt one or both containers along the horizontal axis while the container that is rocked-tilted also moves vertically and cyclically.

Embodiments of the apparatus of the present invention, allows the apparatus to be used to culture animal cells, human cells, insect cells, microbial cells and plant cells. In addition, said apparatus may be used to culture tissues, organs, plant embryos, plantlets and plants.

In a further aspect of the apparatus of the present invention, the first container (1) and the second container (2) have respective filters (14), wherein the filter of each container allows proper aeration, while filtering microscopic contamination. Proper aeration is defined as the supply of a specific mix of oxygen and gases as required by a determined type of culturing e.g., cells.

In one embodiment of the apparatus of the present invention (1), both, the first container and the second container (2), have walls made of a material which is fully transparent to light.

However, in a different embodiment of the apparatus of the present invention, at least one of the two containers, has walls that completely block light passing through said walls, and wherein the container with walls that block passing light is illuminated inside with a source of light with a determined wave length, and wherein all internal surfaces of the container with walls that block passing light are surfaces with the characteristics of a mirror. The source of light can be a light emitting diode, or any other kind of light source. The wave length of the light, e.g., ultraviolet, can be any wave length of the light spectrum. The containers of the apparatus of the present invention can also be adapted for cultures under complete darkness.

In an additional optional aspect of the apparatus of the present invention, the tube (3) that connects the port (4) of the first container (1) to the port (5) of the second container (2) has a filter that allows culture media to pass through, but blocks possible contaminants.

One of the advantages of the apparatus of the present invention is a system of temporal immersion cell culture in which the container can be adapted for any culture surface area size. In addition, the present invention provides homogeneous immersion in the culture media without bubbles, and in the preferred embodiment, a permanent horizontal position resulting in no shearing of the upper cell layer which is critical for delicate cell cultures. Still, the apparatus of the present invention is versatile to allow rocking of one or both containers if desired. The apparatus of the present invention provides a low cost locomotion mechanism that does not require pumps, vacuums or compressed air. In addition any of the two containers of the present invention can be modified to allow for a specific illumination. Since both containers are independent from each other, the first container can be retrieved to change the characteristics of the culture media during different stages of a culture cycle. The embodiment of the apparatus of the present invention, allows the removal of the containers and the tube connecting them, for sterilization.

While the description presents the preferred embodiments of the present invention, additional changes can be made in the form and disposition of the parts without distancing from the basic ideas and principles comprised in the claims.

The invention claimed is:

1. An apparatus for culturing cells comprising:
   A. A first container for holding culture media;
   B. A second container for holding the culturing cells;
   C. At least, one tube that connects a port in the first container to a port in the second container; and,
   D. A mechanism to move the first container vertically and cyclically from a position higher than the second container to a position lower than the second container, and viceversa;
   E. A device to rock-tilt at least one of the two containers along the horizontal axis while said container that is rocked-tilted moves vertically and cyclically;
   wherein the culture media on the first container migrates by gravity to the second container when the first container is in a position higher than the second container, and wherein the culture media migrates back by gravity from the second container to the first container when the first container is in a position lower than the second container; and wherein the first container moves independently from the second container.

2. The apparatus of claim 1, wherein the mechanism to move the first container vertically and cyclically also moves the second container vertically and cyclically, and wherein both containers move independently in a synchronized way such that when one container is up, the other container is down, and viceversa.

3. The apparatus of claim 2, wherein said apparatus comprises a control module to govern the mechanism that moves vertically and cyclically the first container and the second container.

4. The apparatus of claim 1, wherein one of the two containers maintain a horizontally fixed axis position, without tilting from said horizontally fixed axis position when both containers move vertically and cyclically.

5. The apparatus of claim 1, wherein said apparatus is used to culture animal cells, human cells, insect cells, microbial cells and plant cells.

6. The apparatus of claim 1, wherein said apparatus is used to culture tissues, organs, plant embryos, plantlets and plants.

7. The apparatus of claim 1, wherein each of both, the first container and the second container have respective filters, wherein the filter of each container allows proper aeration, while filtering microscopic contamination.

8. The apparatus of claim 1, wherein both, the first container and the second container, have walls made of a material which is fully transparent to light.

9. The apparatus of claim 1, wherein at least one of the two containers, has walls that completely block light passing through said walls, and wherein the container with walls that block passing light is illuminated inside with a source of light with a determined wave length, and wherein all internal surfaces of the container with walls that block passing light are surfaces with the characteristics of a mirror.

10. The apparatus of claim 1, wherein the tube that connects the port of the first container to the port of the second container has a filter.

* * * * *